United States Patent [19]

Krumme et al.

[11] Patent Number: 4,645,489
[45] Date of Patent: Feb. 24, 1987

[54] FLUID DELIVERY APPARATUS WITH SHAPE-MEMORY FLOW CONTROL ELEMENT

[75] Inventors: John F. Krumme, Woodside; Darel E. Hodgson, Palo Alto, both of Calif.

[73] Assignee: Beta Phase, Inc., Menlo Park, Calif.

[21] Appl. No.: 733,036

[22] Filed: Apr. 29, 1985

Related U.S. Application Data

[63] Continuation of Ser. No. 445,390, Nov. 30, 1982, abandoned.

[51] Int. Cl.[4] .............................................. A61M 5/00
[52] U.S. Cl. ................................... 604/65; 604/244; 604/250; 251/11
[58] Field of Search ....................... 251/7-11; 604/34, 65-67, 250, 244

[56] References Cited

U.S. PATENT DOCUMENTS

| 3,403,238 | 9/1968 | Buehler et al. | 251/11 X |
|---|---|---|---|
| 3,613,732 | 10/1971 | Willson et al. | 251/11 X |
| 3,985,134 | 10/1976 | Lissot et al. | 604/34 X |
| 3,990,443 | 10/1975 | Fletcher | 604/65 |
| 3,991,972 | 11/1976 | Eaton | 251/11 |
| 4,105,028 | 8/1978 | Sadlier et al. | 604/65 |
| 4,237,940 | 2/1979 | Faisandier | 137/486 |
| 4,261,388 | 4/1981 | Shelton | 604/65 X |
| 4,265,240 | 5/1981 | Jenkins | 128/214 |
| 4,300,552 | 11/1981 | Cannon | 128/214 |

FOREIGN PATENT DOCUMENTS

| 0062365 | 10/1982 | European Pat. Off. . | |
| 2733702 | 2/1979 | Fed. Rep. of Germany . | |
| 82/01651 | 5/1982 | PCT Int'l Appl. . | |
| 1578741 | 11/1980 | United Kingdom | 251/11 |
| 2054200 | 2/1981 | United Kingdom . | |

OTHER PUBLICATIONS

Journal of Metals, vol. 32, No. 6, Jun. 1980, pp. 129-137, New York, C. M. Wayman: "Some Applications of Shape-Memory Alloys".

Primary Examiner—Dalton L. Truluck
Attorney, Agent, or Firm—Burns, Doane, Swecker & Mathis

[57] ABSTRACT

A unitary disposable conduit extends from the intravenous reservoir along a gravity-flow path to the patient, and incorporates a valve block containing an externally controlled flow-control valve. An electronic controller monitors the drop rate in a drop chamber which is an integral part of the disposable conduit, compares this rate with an operator-selected rate, and controls the valve by varying the current in a shape-memory actuator element whose movements, caused by the resultant Joule heating, are coupled to the valve to proportionally vary the flow rate in the conduit. The valve block is securely received within a recess in the controller, and is automatically coupled to the controller when inserted within this recess. The shape-memory actuator element may be incorporated within the disposable valve block, or may form a part of the controller, with a simple mechanical coupling to transmit its movements to the valve. The valve may be automatically or manually closed when the valve block is removed from the controller, or if power failure occurs.

13 Claims, 9 Drawing Figures

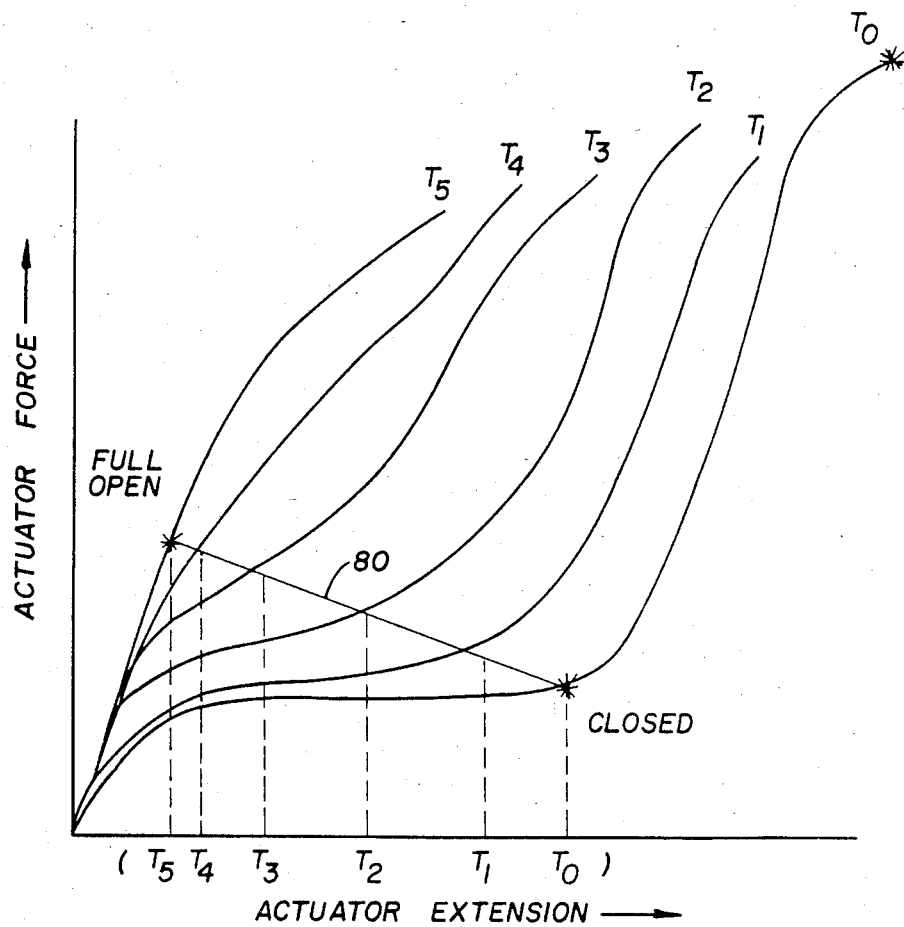

FLUID DELIVERY APPARATUS WITH SHAPE-MEMORY FLOW CONTROL ELEMENT

This is a continuation, of application Ser. No. 445,390, filed Nov. 30, 1982, now abandoned.

BACKGROUND OF THE INVENTION

This invention relates generally to the field of medical appliances, and more particularly to an intravenous flow apparatus. Intravenous flow apparatuses provide a means of administering fluid nutrients and medicaments to medical patients without requiring intervention on the part of the patient and without the delayed incorporation and often destructive modification involved when substances are ingested through the alimentary system of the patient. Consequently, their use in management of trauma in the controlled administration of substances to comatose or otherwise debilitated patients, and in the treatment of a wide range of conditions has become so common as to require no lengthy introduction.

Fundamentally, the systems in use rely principally on gravity flow from a reservoir of liquid suspended above the patient, through a flexible tube terminating in a hypodermic needle inserted into a vein of the patient. Typically, flow rate has been regulated by the use of a relatively primitive roller-clamp which is manually operated by a nurse or other attendant so as to partially occlude the tube leading from the reservoir to the patient to achieve the desired flow rate.

In operating the roller-clamp to regulate flow rate, the nurse observes the rate at which drops emerge from the reservoir into a transparent drop chamber prior to passing through the tube into the patient. By timing the drop-rate, it is possible to achieve regulation of flow rate which is adequate for some purposes.

However, this method of regulation is subject to significant errors both from the difficulty of achieving a desired initial flow rate, and from inevitable long-term changes in the rate.

In particular, the achievement of a desired initial flow rate depends not only on the skill and care of the attendant, but also on the degree to which fine adjustments can be easily secured with the existing apparatus. In this regard, the shortcomings of the relatively primitive roller-clamp make precise control difficult.

Moreover, even when the desired flow rate has initially been achieved, maintenance of this flow rate over a period of an hour or more without further attention and adjustment is highly doubtful. Since the roller-clamp operates by partially occluding the tube passing through it, and since the plastic materials used in forming such tubes are subject to relaxation over a period of time, there will nearly always be some long-term drift in flow rate.

Finally, the necessity to provide frequent attention by highly skilled nurses, and to risk the health of the patient in the event of malfunction of the apparatus are incentives to provide some better and more accurate means of flow regulation.

DESCRIPTION OF THE PRIOR ART

U.S. Pat. No. 4,300,552 issued Nov. 17, 1981 to Cannon, and details an intravenous flow apparatus in which regulation of flow rate is achieved by monitoring drop rate, comparing the rate with a preset value, and correspondingly adjusting a mechanical rotary valve by means of a stepper motor.

U.S. Pat. No. 4,265,240 issued May 8, 1981 to Jenkins, covering an intravenous apparatus for sequentially introducing two or more liquids, such as an antibiotic followed by a saline solution, into the patient's venous system from separate sources without permitting the introduction of air bubbles. Microprocessor control of a corresponding pair of flow regulators or pumps in the two branches of the flow apparatus is provided.

U.S. Pat. No. 4,137,940 issued Feb. 6, 1979 to Faisandier on a flow-control apparatus in which the drop rate is used to control the constriction of a flexible intravenous tube by energizing a motor to mechanically vary the distance separating a pair of constrictor members.

U.S. Pat. No. 3,991,972 issued Nov. 16, 1976 to Eaton, and covers an electrically operated valve in which a flexible tube forming the flow channel is variably constricted by an occlusive constrictor member. Variation of constriction, and hence of flow rate, is achieved by correspondingly varying the current in a heater wire and by coupling the resultant variations in length of the wire to the constrictor member through a motion-multiplying mechanical system.

SUMMARY OF THE INVENTION

An intravenous flow controller according to the present invention uses an optical drop sensor to monitor flow rate, and compact battery-operated electronic circuitry to compare the flow rate with a preselected desired flow rate. An electrical control signal is thus generated for controlling an electrically operated valve of a type which occlusively constricts the flexible intravenous tube a variable desired amount in response to the control signal to produce the desired drop rate.

The essential operating part of the valve is a shape-memory actuator element which is caused to undergo changes in shape in response to corresponding changes in the control signal. The changes in shape of the actuator element produce valve-actuating movement which varies the occlusive constriction of the flexible tube.

The disclosed embodiments all utilize the actuator to move a spring-biased occluding member. A spring driving the occluding member is biased with sufficient force, and in a direction such that it would cause total occlusion of the tube if no opposing force were present. The shape-memory actuator is connected to the spring such that the desired variable changes in shape of the actuator element withdraw the spring by varying amounts from full occlusive contact with the tube, and the amount of occlusion is thus made to depend on the movements of the shape-memory actuator.

The actuator element, which is a simple linear extensor in the disclosed embodiments, is formed of a material possessing the intrinsic property of shape-memory, whereby it can be caused to shorten upon heating and lengthen upon cooling when operating in a temperature actuated transition region. Consequently, the electrical control signal, with suitable current amplification, can control the length of the extensor element and thus operate the valve to control flow, merely by being connected to pass a current through the extensor element corresponding to the desired drop rate. As the current is varied, the temperature of the element is varied by Joule heating to produce a variable force in opposition to the spring force whereby the valve is proportionately opened or closed. In the disclosed embodiments, the spring member is sufficiently strong to elongate the shape-memory actuator element when that element is below its transition temperature and in its weaker state. As the temperature of the actuator element is increased by passing electrical current through it, the shape-memory effect causes the actuator element to proportionately become stronger, and shorten, and thus to move the spring-biased occluding member away from the tube. As the temperature of the actuating element is decreased by reduction of the current passed through it, the shape-memory element cools and becomes weaker and the spring member is able to elongate the actuating element and push the occluding member against the tube, thus closing the valve.

Use of the shape-memory actuator element is a distinct improvement over the use of such actuators as the heater wire in U.S. Pat. No. 3,991,972. The shape-memory actuator has a range of motion which is many times greater yet with similar force levels, and this allows direct valve actuation by the element without a motion multiplying mechanical system. These facts make it simpler, more accurate and more responsive than the patented device. Also, the present device requires fewer moving parts which are sources of error and or failure.

Both the extensor element and spring may be made a part of the disposable intravenous apparatus, or the extensor element may be included within the electronic controller module, with a simple mechanical connection to the spring in the disposable portion. In an alternative and preferred embodiment, both the spring and extensor element remain within the controller such that the disposable portion of the system is as inexpensive as possible.

In the first two of the above arrangements, the tube is automatically fully occluded when the disposable portion of the apparatus is removed from the control unit. In the preferred embodiment, a familiar roller-clamp is provided for terminating flow when desired. All of the embodiments provide that flow is automatically terminated in the event of lost power or the apparatus is turned off.

Full actuation of the valve requires sufficiently little power that the use of penlight batteries or a small rechargeable battery is practicable, and the entire apparatus is thus usable without being connected to power mains.

The above and other features, objects and advantages of the present invention, together with the best mode contemplated by the inventors thereof for carrying out their invention, will become more apparent from reading the following detailed description of preferred and alternative embodiments of the invention while examining the associated drawing, the various figures of which represent:

BRIEF DESCRIPTION OF THE DRAWING

FIGS. 6 and 7 are graphical illustrations of the characteristics of shape-memory materials useful in the present invention.

DETAILED DESCRIPTION OF EMBODIMENTS OF THE INVENTION

Figure 1:
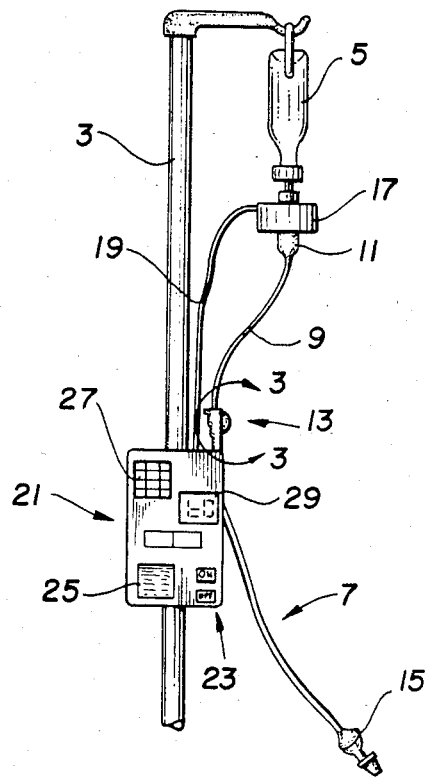
FIG. 1 is an intravenous flow-control apparatus according to the present invention.

In FIG. 1, an intravenous liquid dispensing apparatus 1 designed for intravenous administration of nutrients and medicaments according to the present invention is shown to include a vertical support stand 3, from which is suspended a liquid reservoir 5 in the form of an intravenous fluid bottle. Although reservoir 5 has been illustrated in the form of a bottle, it will be understood that a disposable flexible plastic bag or any other suitable reservoir could be used as well. Since apparatus 1 relies on gravity feed, reservoir 5 is suspended at the upstream end of the apparatus, above a patient (not shown) to whom the contents of the reservoir are to be intravenously administered.

A disposable flow-regulating conduit 7 extending from the reservoir of to the patient forms a unitary, closed, aseptic flow system for conducting the intravenous fluid along a flow path extending from the reservoir to the patient. By thus making every element with which the intravenous fluid comes in contact a part of a single disposable system or conduit, aseptic conditions can be assured in manufacture, without relying on sterilization of any part of the system within the using hospital or other institution. Rather than increasing cost, such a design reduces it, because expensive personnel time need not be wasted in sterilization procedures. Moreover, the risk of contamination is vastly reduced.

Conduit 7 is formed principally of a flexible tube 9, for example of vinyl plastic, of a length sufficient to conveniently extend from reservoir 5 to a patient nearby. A transparent drop chamber 11 is adopted for convenient attachment in fluid communication with the liquid contents of reservoir 5 at the input or upstream end of conduit 7. Tube 9 extends downwardly from the lower end of chamber 11 and passes through a valve block 13, which also forms a part of conduit 7. Within valve block 13, flow rate is controlled as will become clear from the remainder of this description.

Continuing in a downstream direction, tube 9 terminates at an exit point in a hypodermic adapter 15, which serves as a means of connecting disposable conduit 7 to a standard-dimension hypodermic needle which is not shown, but which would be provided in a separate sterile package.

In order to monitor the flow rate through conduit 7, an optical drop sensor 17 is mounted surrounding drop chamber 11. Sensor 17 may contain a lamp and photocell, or a light-emitting diode and photo-diode, paired such that each drop of liquid falling through drop chamber 11 interrupts the path of light between the paired elements and generates a pulse signal in a known manner. A flexible cord 19 connects sensor 17 to an electronic flow controller 21 and provides a means of energizing the light source of sensor 17 and transmitting the resulting drop signal to controller 21.

It will be understood that although a principal purpose of this invention is the regulation and control of flow rate, a parameter having the dimensions of volume of fluid delivered per unit time, the parameter actually monitored and controlled by the embodiments of the invention is drop rate, which has the dimensions of drops of intravenous fluid per unit time. However, these two parameters differ only by the factor of drop volume, which will be assumed for the purposes of the present invention to be approximately constant, at least to the extent of being nearly invariant with time.

Flow controller 21 contains both a battery power supply (not shown) and the necessary electronics to accurately monitor and control flow rate, the control of flow rate being achieved by the connection of valve block 13 to controller 21 as will be discussed with respect to the remaining figures of the drawing. Controller 21 also provides the necessary elements of a user or attendant interface, and is provided for this purpose with an on-off switch 23, an audio alarm 25, such as a loudspeaker of piezo-electric variety, a flow-rate input device 27, such as a hex keypad, and a digital readout device 29, such as a liquid-crystal display, for indicating the measured flow rate.

Figure 2:
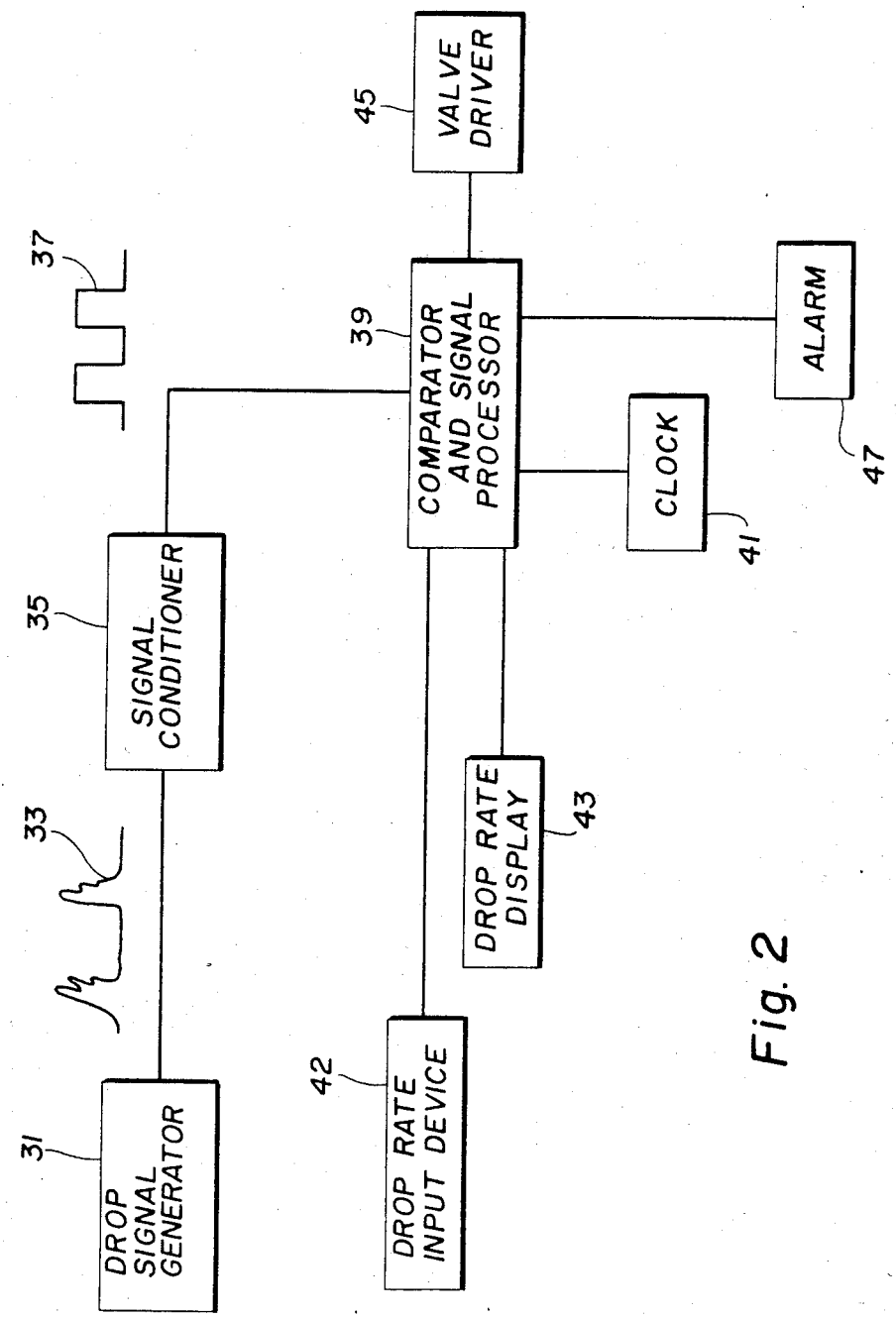
FIG. 2 is a block schematic diagram of the electronic circuitry of an intravenous flow-controller according to the present invention.

Turning now to FIG. 2, a block diagram of the electronics necessary to achieve the functions of controller 21 is shown to include a drop signal generator 31, whose function would be fulfilled by drop sensor 17 in the embodiment of FIG. 1. Since the sort of signal provided by such drop sensors is often somewhat ragged, as illustrated by waveform 33, a signal conditioner 35 is provided for transforming waveform 33 into an idealized square-wave drop-count signal 37. Signal 37 is input to a comparator and signal processor 39.

Processor 39 receives inputs from a clock 41, and from a drop-rate input device 42, which would include the hex keypad or other input device 27 of FIG. 1. Processor 39 compares the user-preselected drop or flow rate with drop-count signal 37 and provides a drop-rate output signal to a drop-rate display 43, and an electrical control input signal to a valve driver 45. The valve driver increases the current output to increase flow rate and decreases current to decrease flow rate, zero flow rate being achieved at or before zero current.

In the event of a malfunction resulting in inability to achieve the correct flow rate, processor 39 also provides an alarm signal to alarm 47, which would include the audio alarm 25 in FIG. 1. Valve driver 45 conditions the control input signal from processor 39 to produce at the output of driver 45 a valve control signal capable of driving the flow-control valve associated with valve block 13, and would in general include a current-amplifier.

Within the context of the present invention, the electronic circuitry of FIG. 2 serves as a flow-rate monitor and control means which monitors flow rate along the unitary flow path extending from reservoir 5 to the patient, and derives from the monitored rate a valve control signal which is directly related to the difference between monitored flow rate and the rate preselected at input device 42. The system details may be as disclosed in U.S. Pat. No. 4,137,940.

Although the valve control signal output from valve driver 45 might, accordingly, be proportional to the difference between the monitored and preselected flow rates, other signal relationships such as logarithmic also fall within the scope of the invention. Consequently, the phrase "directly related" in this context is to be taken to mean whatever signal relationship is necessary to drive the flow-control valve associated with valve block 13 in a sense to reduce a disparity between monitored and preselected flow rates.

Figure 3B:
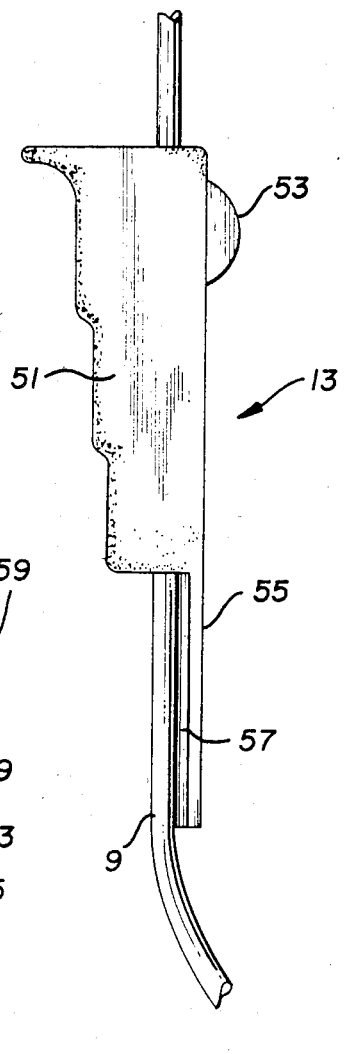
FIG. 3 is an exploded view, partially cut away, showing a preferred embodiment of the portion of the apparatus of FIG. 1 within the arrows 3—3.
Figure 3A:
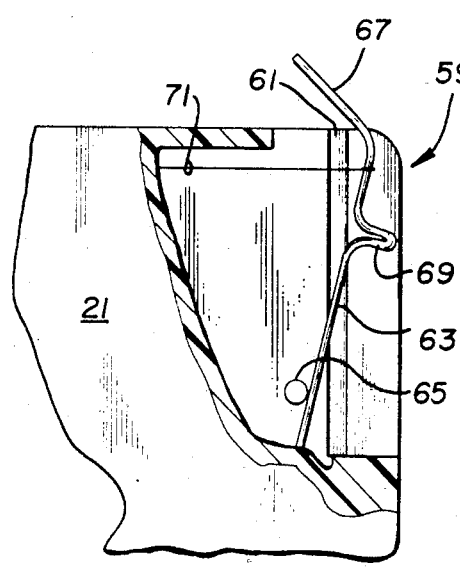

FIGS. 3a-b illustrates a preferred embodiment of the portion of FIG. 1 within the arrows 3—3. In particular, FIG. 3b shows the details of an electrically operated valve means disposed along the flow path from reservoir 5 to the patient. In accordance with the present invention, such a valve means responds to the valve control signal output from valve driver 45 of FIG. 2 by varying flow rate along the flow path in direct relation to the control signal.

In FIG. 3b, valve block 13 is provided with a housing 51 of molded plastic, for example, having a thumb-operated shutoff roller 53 which may be rolled upwardly or downwardly to variably occlude tube 9, permitting manual adjustment of flow rate when desired. As far as presently described, the embodiment of FIG. 3 is the well known roller clamp in widespread use in hospitals.

However, valve block 13 of FIG. 3b also provides for automatic, continuously monitored control of flow rate in accordance with the present invention, through the provision of a mounting tongue 55 projecting from the lower edge of block 13. As shown, tongue 55 includes a pair of vee-shaped or dovetail mounting rails 57, only one of which is shown, extending vertically along its sides. Valve block 13 is securely received within a recess 59 provided with correspondingly shaped grooves 61 within controller 21.

As seen in FIG. 3b within recess 59, flow rate is varied and controlled by compressively occluding the portion of tube 9 lying in contact with tongue 55, which serves in this regard as a rigid backer member to support tube 9. For this purpose, a spring-biased occluding member 63, together with a stop pin 65 is provided. Member 63 may be formed of a resilient material such as beryllium copper or stainless steel by a series of punching, bending and folding operations, and may be provided in this way with a thumb-tab 67 for manually withdrawing member 63 from contact with tube 9 when desired. Member 63 is provided with a convex occluding projection 69 which presses into and occludes tube 9 in order to control flow.

Stop pin 65 is positioned so as to create sufficient force through flexure of member 63 to fully occlude tube 9 in the absence of an opposing force. In accordance with the present invention, a shape-memory valve actuator element 71 is provided for withdrawing member 63 from full occlusive contact with tube 9 in order to provide the variable, partial occlusion needed to adequately control flow.

Actuator element 71 may be a single strand of wire of a shape-memory material, or it may preferably be a loop of such wire, extending around member 63 and terminating at the left in FIG. 3 by attachment to a pair of electrical contacts (not shown). In either case, element 71 may be made of a suitable shape-memory material such as one of the nickel-titanium alloys known under the trade name Nitinol, and may have a diameter of 0.005 to 0.010 inch, for example.

Shape memory materials such as the Nitinol alloys are characterized by the ability to transit between two crystalline states, such as between the austenitic and martensitic states, whenever their temperature is caused to pass through a certain region of transition temperatures. Moreover, strain of such materials produced in the lower temperature state can be substantially fully recovered by transition to the higher temperature state.

Consequently, actuator element 71 may be stretched while in its low temperature martensitic state prior to being connected to member 63. Upon subsequent heating to the high temperature austenitic phase, the element 71 will recover to its initial length, and the resultant motion can be employed to move member 63 progressively, resulting in controllable valve actuation.

Although the requisite heating of member 71 in response to a control signal could be obtained with a separate, indirect heater energized with the output signal from valve driver 45 in FIG. 2, in accordance with the present invention, such heating can be more efficiently secured by producing a current directly in member 71, which is then heated by the resultant Joule dissipation in proportion to the square of the current.

In the context of the present invention, a means to cause heating of a shape-memory valve actuating member such as member 71 in response, to the valve control signal produced by valve driver 45 might comprise a separate, indirect heater placed close to the valve-actuating member and energized with the valve control signal, or might simply comprise the necessary electrical contacts and connections to form the valve actuating member into a circuit connected directly, inductively, or otherwise to the output of valve driver 45.

Figure 4A:
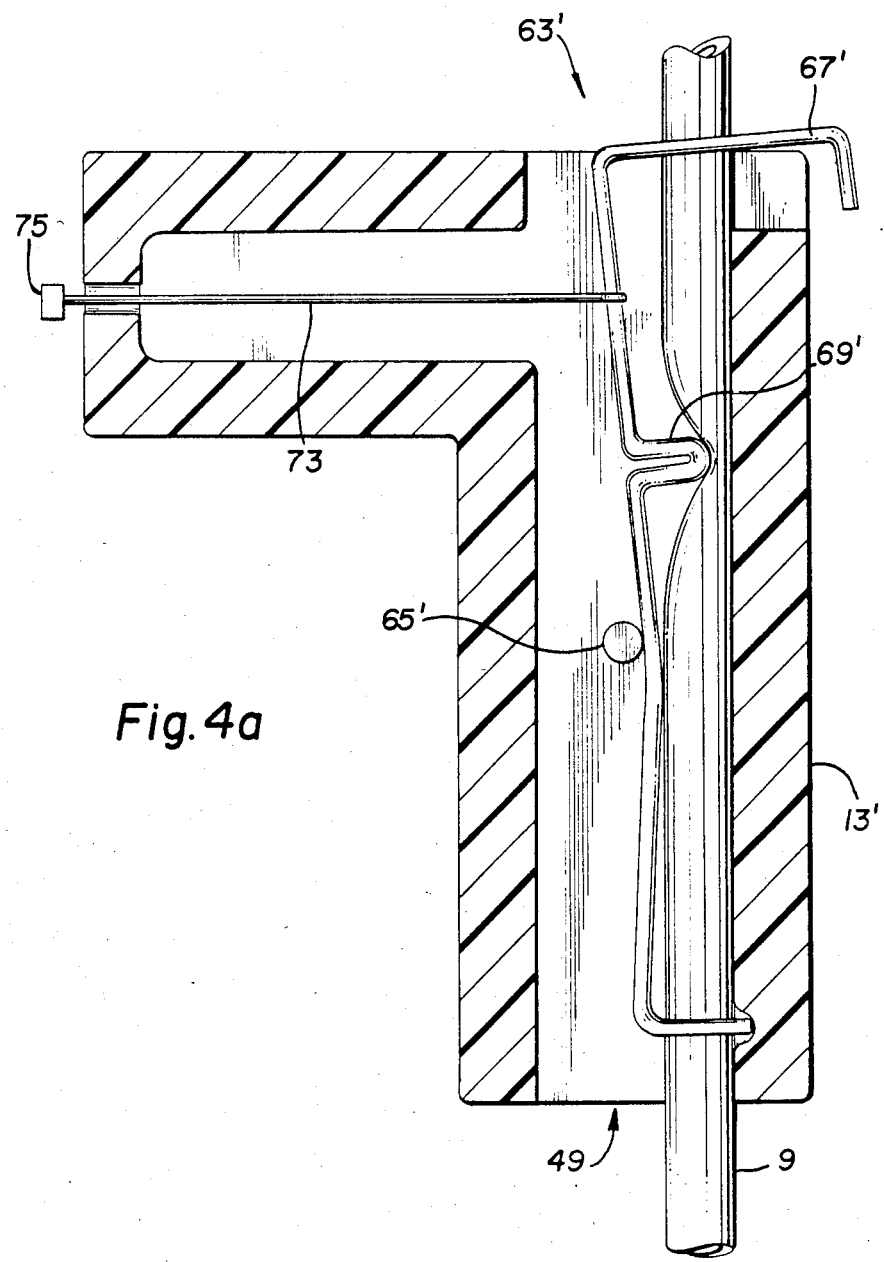
FIG. 4a-b are side sectional views of alternative embodiments of the apparatus of the present invention.
Figure 4B:
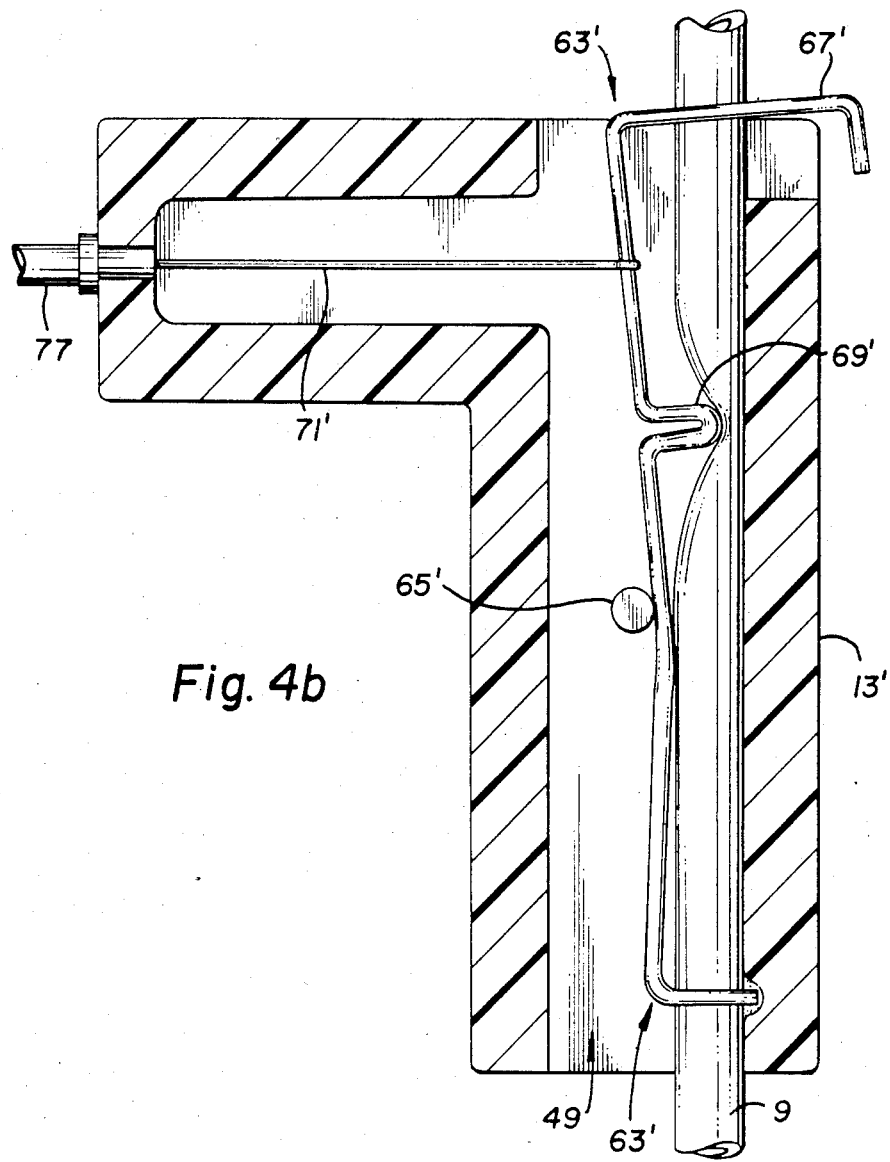

In FIGS. 4a-b, alternative embodiments in which at least a portion of the valve structure has been mounted within a modified valve block 13' are illustrated. These valve structures according to the present invention are illustrated as they would appear in cross-section within valve block 13'. In each embodiment, a central bore 49 extends vertically through block 13 for receiving tube 9 passing therethrough.

In the embodiments of FIGS. 4a-b, a spring-biased occluding member 63 similar to member 63 of FIG. 3a is provided. As before, a stop pin 65 serves to bias member 63 through flexure sufficiently to fully occlude tube 9 in the absence of any countervailing force while a thumb-tab 67 similar to the thumb-tab 67 of FIG. 3a is provided for manually withdrawing member 63 from full occlusion of tube 9 for priming the system, for example. Since tube 9 is fully occluded by member 63 unless withdrawn, the production and control of the requisite flow rate in the system obviously requires some means of progressively withdrawing member 63 from its position of full occlusion.

In the embodiment of FIG. 4a, such a means has been provided in the form of a draw-rod 73 having one end attached to member 63, as by being looped therearound, and extending leftwardly in FIG. 4a through an aperture in block 13' to terminate in an enlarged end portion 75. Alternatively, member 63 could have been provided during manufacture with a projection shaped like draw-rod 73. By means of end 75, rod 73 may be drawn to the left by a suitable movable actuator located within controller 21.

In accordance with the present invention, such a movable actuator may include, as the motion-producing element, a shape-memory element, which would be physically located within controller 21 in the event that the valve mechanism of FIG. 4a is to be employed. However, the shape-memory element may also be incorporated within the disposable valve mechanism, to operate directly upon spring-biased member 63, as in FIG. 4b.

FIG. 4b employs the same structure as FIG. 4a with the exception that the means for applying a force to member 63 to cause progressive opening of the valve is a shape-memory element 71', similar to the element 71 of FIG. 3a. That is element 71' is either a single strand or a loop of wire, as of 0.005 to 0.010 inch diameter, made of a material having the intrinsic property known as shape memory.

Element 71 is preferably formed into a loop extending at the right in FIG. 4b around member 63, and terminating at the left in a pair of electrical contacts 77, only one of which is shown, the other being behind the contact 77 illustrated in the drawing. As in the case of FIG. 3a, by producing and controlling a current through this loop, the extensor element can be caused to lengthen and shorten to produce controlled valve actuation merely by control of the energizing current as by the circuit of FIG. 2.

Figure 5:
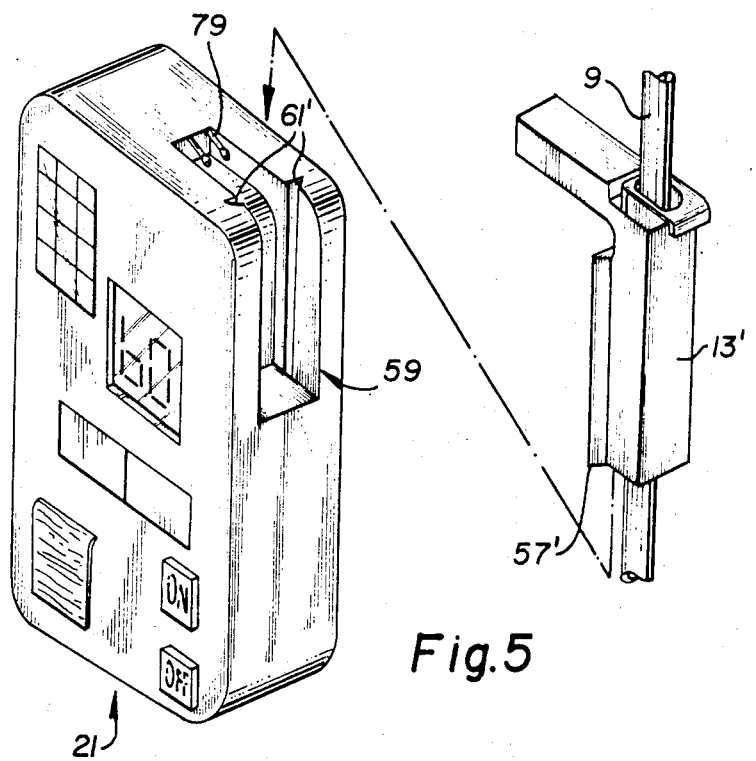
FIG. 5 is an exploded perspective view of one embodiment of intravenous flow-controller according to the present invention.

Similarly, in the case of FIG. 4a, the requisite movement of member 63 may be secured by placing the shape-memory extensor element in controller 21, with mechanical means to couple the resultant movements to draw rod 73. Turning to FIG. 5, the means of receiving block 13 of FIG. 4a or 4b operatively within the housing of controller 21 are shown to comprise a correspondingly-shaped recess 59 in the side of controller 21. A pair of vee-shaped or dovetail grooves 61, and a correspondingly-shaped pair of rails 57 on block 13 provide a secure connection.

A pair of electrical contactors 79 are provided for mating with contacts 77 in the embodiment of FIG. 4b. Although not shown, any suitable known means of securely grasping end portion 75 of the embodiment of FIG. 4a could have been provided in place of contactors 79.

Figure 6:
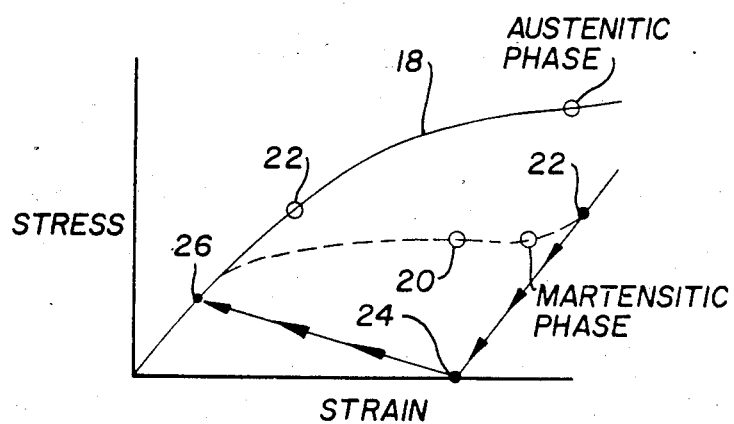

FIG. 6 is a generalized stress-strain diagram of the class of materials known as shape-memory materials. Such materials are characterized by having a low-temperature martensitic phase illustrated by characteristic 18 in FIG. 6, and a high-temperature austenitic phase illustrated by characteristic 20 in FIG. 6, and by the ability to transit between the very different physical characteristics of these two phases whenever their temperature passes through a certain range of transition temperatures which is an intrinsic characteristic of the material.

In particular, if such materials are cooled below the transition temperature such that they are in the martensitic phase, and are then stressed sufficiently to physically deform them into what is an apparently permanent new shape, upon heating above the transition temperature, all of the deformation which occurred in the martensitic phase will be reversed, and the original shape will be recovered. That is, the deformed object will simply revert to the shape in which it existed prior to the cycle of cooling, deformation and reheating.

In accordance with the present invention, particularly good use of this characteristic can be made by employing shape-memory material to form a valve actuator element, such as actuator elements 71 or 71' of FIGS. 3a and 4b, respectively. By stretching these elements while they are in their low-temperature martensitic phase, they will contract to their unstretched length whenever their temperature is raised through the transition temperature range. The resulting movement can be employed to operate a variable constriction valve as in the already described embodiments.

FIG. 6 shows the relationships between stress and strain involved in such a use of shape-memory materials. If the extensor element has been formed of the material of FIG. 6 and is then stretched while at a temperature below the transition temperature, the stress-strain relationship is depicted by characteristic 18, labeled "Martensitic Phase" in FIG. 6.

During the deformation involved in stretching the actuator element, the shape-memory material under-goes increasing stress and strain until, at point 22, the resulting deformation is sufficient and the stress is removed. Stress thereupon goes to zero, and strain or deformation recovers by a small amount, leaving the material in the condition represented by point 24.

If the actuator element is subsequently reheated above the transition temperature such that the material is caused to enter the austenitic phase, strain will recover along the abscissa (which is the locus of zero-stress conditions) until the austenitic phase characteristic is reached, and would actually reach the origin in the total absence of any mechanical constraints.

However, some stress will be present because of the force exerted by spring-biased occluding member 63 and 63' in FIGS. 3a and 4a-b, such that the equilibrium stress-strain state may be represented by point 26 on charactistic 20. As FIG. 6 shows, point 26 is actually quite close to the origin, such that the actuator element has very nearly fully recovered to its initial length.

Reference is now made to FIG. 7 wherein is illustrated typical force vs. extension characteristics of the mechanism of the invention at different temperatures $T_0$-$T_5$. At $T_0$, it is assumed that a control current flows that maintains the temperature of the linear extension element below the transition temperature, i.e., in the martensitic phase. Thus the wire 71' in FIG. 4b is fully extended under force of the spring actuator 63' and the tube 9 is blocked. At temperature $T_5$, the wire 71' has achieved its austenitic phase, the wire achieves its initial length, raises the spring actuator 63' and the tube 9 is fully open. At any of the intermediate temperatures $T_1$-$T_4$, the extension of the wire 71' is decreased to the extent illustrated along extension line 80 and the tube 9 is blocked or unblocked to the degree corresponding to the illustrated extension. The current output from valve driver 45 will remain constant only when the drop rate produced equals the drop rate desired.

Although the illustrated embodiments have all employed a linear extensor element in combination with an opposing spring, the invention is not so limited. Many other geometries employing a shape-memory actuator element will suggest themselves to workers skilled in the art. Such geometries as a curved shape-memory actuator element having different radii of curvature in its two phases could be used as well. The actuator element need not operate to constrict the flexible tube through the intermediary element of an occluding member as it does in the disclosed embodiments, but may operate directly upon the tube to achieve the necessary occlusion and flow control.

Moreover, a linear extensor element could be fabricated in such a way that it lengthens, and pushes rather than pulls an opposing spring as temperature rises through the transition range. All such embodiments fall within the purview of this specification, and within the scope of our invention.

Also, in FIG. 7 is shown flow rate versus temperature for a typical flow-rate controller employing an extensor element made of a binary or ternary compound of nickel and titanium having a transition temperature range of 60-80 degrees Celsius in the absence of stress. In particular, a useful compound of this sort would be a binary composition having from 49.5 to 51.0 atomic % of nickel.

The effect of the stress provided by member 63 on extensor element 71, is that the transition temperature range has been enlarged to extend approximately between temperatures T1=50 and T2-100 degrees Celsius. As the temperature of the extensor element will vary as a monotonically increasing function of the electrical current used to heat it, one can see how the electronic monitoring and control device of FIG. 2 would variably adjust the flow-rate controlling apparatus to give any desired flow rate.

It is noteworthy that the relationship between temperature and flow rate is subject to a hysteresis effect. The temperature of the extensor required for an arbitrary flow rate is higher if the extensor temperature is achieved by heating up to the arbitrary flow rate than it is by cooling downward to the arbitrary flow rate. This effect can be used to advantage to minimize power useage in the extensor by designing the electronic controller to adjust flow rate by approaching the proper temperature of the extensor from above rather than below. Since the same flow rate can be achieved this way at a lower extensor temperature, less current and, hence, less power is required in the extensor wire to achieve the desired flow rate.

In operation, I have found that a Nitinol wire having a length of 1.5 to 2.0 inches, and a resistance of approximately 4 ohms can be employed as the extensor element with currents approximating 150 mA, such that power consumption is less than 100 mW, and with a resultant accuracy of drop rate control of considerably better than 5%.

Although this invention has been described with some particularity with respect to a specific set of embodiments which, taken together, comprise the best mode known to the inventors for carrying out their invention, it will be understood that many changes could be made, and many alternative embodiments thus derived, without departing from the scope of the invention. Consequently, the scope of the invention is to be determined only from the following claims:

We claim:

1. An intravenous flow controller for use in a gravity-fed intravenous liquid dispensing apparatus designed for intravenous adminstration of nutrients and medicaments at a preselected flow rate from a liquid reservoir at an upstream end thereof, downwardly along a flow path bounded over a portion of its length by a flexible intravenous tube, to a point of exit therefrom, said flow controller comprising:

flow-rate monitor and control means for monitoring the flow rate along said flow path and for producing in response to said flow rate an electrical valve control signal directly related to the difference between said flow rate and said preselected flow rate;

valve means disposed along said flow path and connected to respond to said electrical valve control signal by varying said flow rate in response thereto in direct relation to the magnitude of said valve control signal, said valve means comprising:

means for biasing said valve means to a closed position to prevent flow of liquid through the flexible intravenous tube, a shape-memory valve actuator element connected to actuate said valve means and made of a material which has the intrinsic property of shape memory and transits between two different crystalline phases whenever its temperature passes through a certain region of transition temperatures, said actuator element having a first physical shape defined by a first set of dimensions at temperatures above said transition temperature and a second physical shape defined by a second set of dimensions at temperatures below said transition temperature, and transiting through a region of shapes intermediate said first and second shapes as its temperature passes through said region of transition temperatures, and causing flow rate along said flow path to vary in response to said transiting through said region of transition temperatures;

means to cause heating of said actuator element to change its temperature in direct relation to the magnitude of said valve control signal, whereby changes in physical shape of said actuator and, hence, flow rate are caused by changes in said valve control signal;

said shape memory valve actuator overcoming said biasing means and causing opening of said valve means to permit flow of fluid only upon heating of said actuator above a prescribed minimum temperature.

2. A disposable flow-regulating conduit for use in a gravity-fed intravenous liquid dispensing apparatus designed for intravenous adminstration of nutrients and medicaments at a preselected flow rate from a liquid reservoir at an upstream end thereof, downwardly along a flow path bounded over a portion of its length by a flexible intravenous tube, to a point of exit therefrom, said apparatus including flow-rate monitoring and control means to monitor the flow of liquid downwardly along said flow path and to produce in response to the monitored flow rate an electrical control signal directly related to the difference between the monitored flow rate and the preselected flow rate, said flow-regulating conduit comprising;

a flexible tube of a length for extending generally from said reservoir to said point of exit;

reservoir attachment means at an upstream end of said conduit for attachment to said reservoir and for communicating fluid downstream therefrom through said flexible tube;

electrically operated valve means disposed along said flow path and electrically connected to response to said electrical control signal by varying said flow rate in response thereto in direct relation to the magnitude of said control signal, said electrically operated valve means comprising;

a valve having means for occluding said flexible tube to prevent liquid flow therethrough, said valve having means to bias said valve to occlude said flexible tube, a shape-memory valve actuator element connected to operate said means for occluding and made of a material which has the intrinsic property of shape memory and transits between two different crystalline phases whenever its temperature passes through a certain region of transition temperatues, said actuator element having a first physical shape defined by a first set of dimensions at temperatures above said transition temperature and a second physical shape defined by a second set of dimensions at temperatures below said transition temperature, and transiting through a region of shapes intermediate said first and second shapes as its temperature passes through said region of transition temperatures, and causing flow rate along said flow path to vary in response to said transiting through said region of transition temperatures;

means to cause heating of said actuator element to change its temperature in direct relation to the magnitude of said electrical control signal;

said shape-memory valve actuator opposing the force of said means to bias from its second physical shape to its first physical state.

3. The apparatus of claim 1 or 2 wherein said electrically operated valve means comprises occluding means coupled to said actuator element movement to compressively occlude said flexible tube over a certain region thereof in direct relation to the relative movement of said one portion of said actuator element to thereby control flow rate through said tube.

4. The apparatus of claim 3 wherein said actuator element is operatively connected to said occluding means to cause full occlusion of said tube when said actuator element is in one of its said phases, and to progressively withdraw said occluding means from full occlusion of said tube as said actuator element transits to the other of its said phases.

5. The apparatus of claim 1 or 2 wherein said means to cause heating in direct relation to the magnitude of said valve control signal includes means to cause an electric current to flow in said actuator element in direct relation to the magnitude of said valve control signal, to thereby cause Joule heating of said actuator element in direct relation to said valve control signal.

6. The apparatus of claim 1 or 2 wherein said electrically operated valve means comprises bias means connected to said actuator element to exert a force on said one portion thereof along the direction of relative movement of said one portion.

7. The apparatus of claim 6 wherein said force exerted by said bias means is in a direction to aid said relative movement when the temperature of said actuator element transits from above said transition temperature to below said transition temperature.

8. The apparatus of claim 1 or 2 wherein said shape-memory actuator element includes a shape-memory extensor element having a greater length at temperatures below a certain transition temperature range, and a lesser length at temperatures above said transition temperature range, and wherein said electrically operated valve means includes occluding means coupled to said extensor element to cause occlusion of said flexible tube in direct relation to the legnth of said extensor element, to fully occlude said tube at temperatures below said transition temperature range, and to progressively reduce the occlusion of said tube at temperatures above said transition temperature range.

9. The flow-regulating conduit of claim 8 wherein said occluding means comprises a spring-biased occluding element connnected to said extensor element, said spring-biased element being biased in a direction to occlude said tube, and being withdrawn from said occlusion upon transition of said extensor element from said greater to said lesser length.

10. A flow rate controller for use in gravity-fed liquid dispensing apparatus, comprising:

means defining a gravity feed flow path between a reservoir and a point of utilization of liquid;

a valve having a member movable between a first position locking flow of a liquid along said flow path and a second position permitting generally uninhibited flow of a fluid along said flow path;

means exerting a force for biasing said member to said first position; and a shape-memory element of a material having the intrinsic property of shape-memory and which transits between two different shape defining a first shape at a first temperature and a second shape at a second temperature and transiting through all intermediate shapes over the temperature range between between said first and second temperatures, said shape-memory element overcoming said force of said biasing means upon transiting from the lower to the higher of said first and second temperatures.

11. A flow rate controller as in claim 10 wherein said means exerting a force comprises a spring member exerting a force on said movable member to close said flow path and wherein said shape-memory element comprises a thin wire connected between said movable member and a relatively fixed location.

12. A flow rate controller as in claim 11 wherein said spring member comprises a cantilevered spring having one end secured against movement and another end free to move, said movable member located adjacent said free end and said thin wire connected to said cantilevered spring adjacent to said free end.

13. A flow rate controller as in claim 12 further including means for applying a force to said cantilevered spring intermediate said secured and free ends of said cantilevered spring.

* * * * *